(12) United States Patent
Rockrohr

(10) Patent No.: US 11,259,861 B2
(45) Date of Patent: Mar. 1, 2022

(54) COMMON CONNECTOR FOR MONOPOLAR AND BIPOLAR INSTRUMENTS

(71) Applicant: Covidien LP, Mansfield, MA (US)

(72) Inventor: Brian Rockrohr, Guilford, CT (US)

(73) Assignee: COVIDIEN LP, Mansfield, MA (US)

( * ) Notice: Subject to any disclaimer, the term of this patent is extended or adjusted under 35 U.S.C. 154(b) by 704 days.

(21) Appl. No.: 16/073,560

(22) PCT Filed: Feb. 22, 2017

(86) PCT No.: PCT/US2017/018798
§ 371 (c)(1),
(2) Date: Jul. 27, 2018

(87) PCT Pub. No.: WO2017/147106
PCT Pub. Date: Aug. 31, 2017

(65) Prior Publication Data
US 2019/0059975 A1 Feb. 28, 2019

Related U.S. Application Data

(60) Provisional application No. 62/298,498, filed on Feb. 23, 2016.

(51) Int. Cl.
*A61B 18/12* (2006.01)
*A61B 34/30* (2016.01)
(Continued)

(52) U.S. Cl.
CPC .......... *A61B 18/1206* (2013.01); *A61B 18/16* (2013.01); *A61B 34/30* (2016.02);
(Continued)

(58) Field of Classification Search
CPC ...... A61B 18/1206; A61B 2018/00916; A61B 2018/0922; A61B 2018/00928;
(Continued)

(56) References Cited

U.S. PATENT DOCUMENTS 4,171,700 A * 10/1979 Farin .................. A61B 18/1233
606/34
5,472,442 A * 12/1995 Klicek ............... A61B 18/1482
606/34
(Continued)

FOREIGN PATENT DOCUMENTS

EP 2529687 A2 12/2012
EP 2866713 A1 5/2015
(Continued)

OTHER PUBLICATIONS

International Search Report and Written Opinion corresponding to counterpart Int'l Appln No. PCT/US17/018798 dated May 30, 2017.
(Continued)

*Primary Examiner* — Ronald Hupczey, Jr.

(57) ABSTRACT

An electrosurgical system includes an electrosurgical instrument and an electrosurgical generator. The generator includes an energy source having an active terminal and a return terminal that outputs electrosurgical energy and a controller that controls the energy source. A cable is coupled between the electrosurgical instrument and the electrosurgical generator where the cable includes a first conductor and a second conductor. The controller is configured to electrically couple the active terminal and/or the return terminal to the electrosurgical instrument using the first conductor and/or the second conductor based on whether the electrosurgical instrument is a monopolar instrument or a bipolar instrument.

20 Claims, 4 Drawing Sheets

(51) Int. Cl.
  *A61B 34/37* (2016.01)
  *A61B 34/00* (2016.01)
  *A61B 90/50* (2016.01)
  *A61B 18/16* (2006.01)
  *A61B 18/00* (2006.01)
  *A61B 17/00* (2006.01)

(52) U.S. Cl.
  CPC .............. *A61B 34/37* (2016.02); *A61B 34/76* (2016.02); *A61B 90/50* (2016.02); *A61B 2017/00115* (2013.01); *A61B 2017/00477* (2013.01); *A61B 2018/00178* (2013.01); *A61B 2018/00702* (2013.01); *A61B 2018/126* (2013.01); *A61B 2018/1253* (2013.01)

(58) Field of Classification Search
  CPC ........... A61B 2018/00957; A61B 2018/00988; A61B 2018/1246
  See application file for complete search history.

(56) References Cited

U.S. PATENT DOCUMENTS

| | | | |
|---|---|---|---|
| 5,562,503 A * | 10/1996 | Ellman | A61B 18/14 200/51.03 |
| 6,113,596 A * | 9/2000 | Hooven | A61B 18/14 606/42 |
| 6,836,688 B2 | 12/2004 | Ingle et al. | |
| 6,875,182 B2 | 4/2005 | Wardle et al. | |
| 7,674,261 B2 * | 3/2010 | Garito | A61B 18/12 606/42 |
| 8,998,891 B2 | 4/2015 | Garito et al. | |
| 9,050,089 B2 | 6/2015 | Orszulak | |
| 9,445,863 B2 * | 9/2016 | Batchelor | A61B 18/1442 |
| 2005/0004634 A1 | 1/2005 | Ricart et al. | |
| 2009/0062786 A1 | 3/2009 | Garito et al. | |
| 2009/0248041 A1 * | 10/2009 | Williams | A61B 8/4488 606/130 |
| 2012/0310241 A1 | 12/2012 | Orszulak | |
| 2014/0276772 A1 | 9/2014 | Batchelor et al. | |
| 2014/0276797 A1 | 9/2014 | Batchelor et al. | |

FOREIGN PATENT DOCUMENTS

| | | |
|---|---|---|
| JP | 2009056308 A | 3/2009 |
| JP | 2012250039 A | 12/2012 |
| KP | 10-0879617 | 1/2009 |
| WO | 2009142393 A2 | 11/2009 |
| WO | 2014152108 A1 | 9/2014 |
| WO | 2017147106 A1 | 8/2017 |

OTHER PUBLICATIONS

Extended European Search Report dated Aug. 29, 2019 corresponding to counterpart Patent Application EP 17757092.6.
Chinese First Office Action dated Jul. 22, 2020 corresponding to counterpart Patent Application CN 201780011641.9.
Japanese Office Action dated Jan. 20, 2021 corresponding to counterpart Patent Application JP 2018 542174.
Chinese Second Office Action dated Dec. 30, 2020 corresponding to counterpart Patent Application CN 201780011641.9.
Chinese Third Office Action dated Apr. 16, 2021 corresponding to counterpart Patent Application CN 201780011641.9.
Indian Office Action dated May 17, 2021 corresponding to counterpart Patent Application IN 201817032420.
Japanese Office Action dated Jun. 2, 2021 corresponding to counterpart Patent Application JP 2018-542174.

* cited by examiner

COMMON CONNECTOR FOR MONOPOLAR AND BIPOLAR INSTRUMENTS

CROSS-REFERENCE TO RELATED APPLICATIONS

This application is a U.S. National Stage Application filed under 35 U.S.C. § 371(a) of International Patent Application Serial No. PCT/US2017/018798, filed Feb. 22, 2017, which claims the benefit of and priority to U.S. Provisional Patent Application Ser. No. 62/298,498, filed Feb. 23, 2016, the entire disclosure of which is incorporated by reference herein.

BACKGROUND

Electrosurgery involves application of high radio frequency electrical current to a surgical site to cut, ablate, or coagulate tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated. A patient return electrode is placed remotely from the active electrode to carry the current back to the generator.

In bipolar electrosurgery, one of the electrodes of the hand-held instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes. When the electrodes are sufficiently separated from one another, the electrical circuit is open and thus inadvertent contact of body tissue with either of the separated electrodes does not cause current to flow.

Because monopolar and bipolar tools are structurally different in the way the deliver electrical current to a target tissue, different cables and/or connectors are needed to connect the tools to a source of electrical current. Therefore, there is a need to simplify the workflow and eliminate the need for separate cables and/or connectors when switching from a monopolar tool to a bipolar tool.

SUMMARY

The present disclosure is directed to a common connector for electrosurgical instruments, and, more specifically, a common two conductor connector capable of connecting a monopolar tool or a bipolar tool to a source of electrosurgical energy.

In an aspect of the disclosure, an electrosurgical system is provided that includes an electrosurgical instrument and an electrosurgical generator. The electrosurgical generator includes an energy source having an active terminal and a return terminal that outputs electrosurgical energy and a controller that controls the energy source. A cable electrically couples the electrosurgical instrument to the electrosurgical generator where the cable includes a first conductor and a second conductor. The controller is configured to electrically couple the active terminal and/or the return terminal to the electrosurgical instrument using the first conductor or the second conductor based on whether the electrosurgical instrument is a monopolar instrument or a bipolar instrument.

In some embodiments, the controller electrically couples the return terminal to a return pad when the electrosurgical instrument is the monopolar instrument. The return terminal is electrically coupled to the return pad based on a signal transmitted along the second conductor from the monopolar instrument or based on a user input.

In some embodiments, the electrosurgical system also includes a first switch and a second switch. The first switch electrically couples the return terminal to the return pad and the second switch electrically couples the second conductor to the controller when the electrosurgical instrument is the monopolar instrument. The first switch and the second switch couple the return terminal to the second conductor when the electrosurgical is the bipolar instrument. The first switch and/or the second switch may be controlled by the controller based on data from the electrosurgical instrument.

In some embodiments, the second conductor is coupled to the controller when the monopolar instrument is connected to the electrosurgical generator.

In some embodiments, the controller electrically couples the return terminal to the electrosurgical instrument using the second conductor when the electrosurgical is the bipolar instrument.

In some embodiments, the electrosurgical system includes a demultiplexer. The demultiplexer: demultiplexes an incoming signal including the electrosurgical energy and a data signal from the bipolar instrument when the bipolar instrument is connected to the electrosurgical generator; provides the data signal to the controller; and returns the electrosurgical energy to the energy source.

In some embodiments, the controller electrically couples the return terminal to the second conductor based on a signal from the bipolar instrument o a user input.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

The present disclosure is directed to a common two conductor connector for electrosurgical instruments. The connector permits a user or clinician to use the same connector for both monopolar and bipolar instruments. When the connector is used to connect a monopolar instrument to a source of electrical current, e.g., an electrosurgical generator, one conductor is used to transmit monopolar energy to the instrument while the other conductor is used to transmit and/or receive information between the electrosurgical generator and the monopolar instrument. When the connector is used to connector a bipolar instrument to the electrosurgical generator, both conductors are used to transmit bipolar energy to the bipolar instrument.

Figure 1:
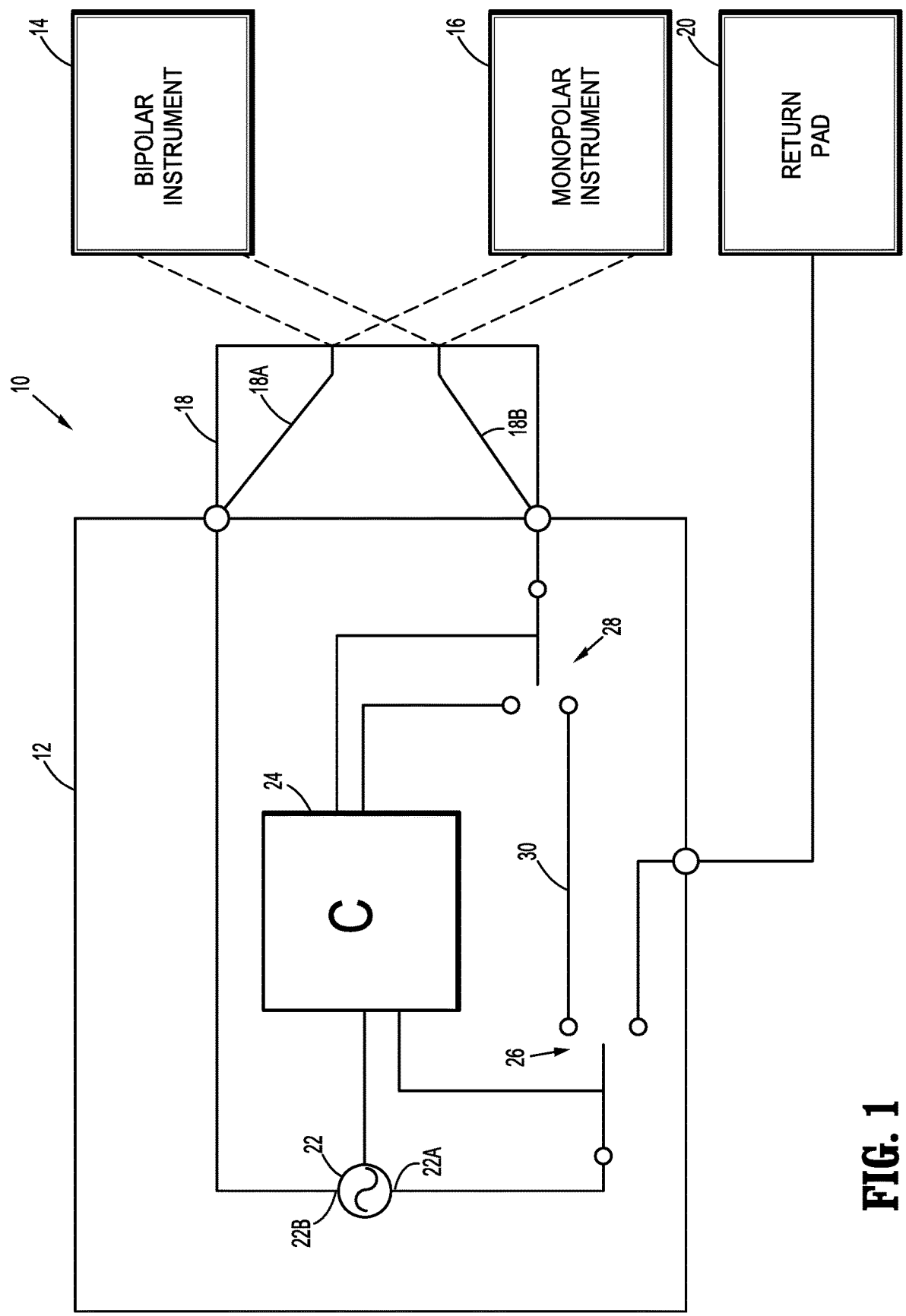
FIG. 1 is a block diagram of an electrosurgical system using a common conductor in accordance with an embodiment of the present disclosure.

Turning to FIG. 1, an electrosurgical system in accordance with an embodiment of the present disclosure is shown generally as 10. Electrosurgical system 10 includes an electrosurgical generator 12 that may be connected to a bipolar instrument 14 or a monopolar instrument 16 via cable 18 that has one end that is connected to electrosurgical generator 12 via conventional means and the other end is connected to either the bipolar instrument 14 or the monopolar instrument 16 via conventional means. The cable 18 includes two conductors 18A and 18B. Conductors 18A and 18B may be arranged side by side or they may be coaxial with each other. A dielectric or insulative material (not shown) may be electrically isolate conductor 18A from conductor 18B. A return pad 20 may be connected to the electrosurgical generator 12 when the monopolar instrument 16 is connected to the electrosurgical generator 12.

The electrosurgical generator 12 includes an energy source 22, which may provide radio frequency (RF) or microwave energy. A controller 24 controls the output of energy source 22 based on the type of therapy (i.e., sealing, cutting, cauterizing, etc.) being applied to tissue by the instrument 14 or 16.

When the monopolar instrument 16 is connected to the electrosurgical generator 12, the controller 24 actuates switch 26 to connect a return terminal 22A of the energy source 22 to the return pad 20 while switch 28 is actuated to connect the conductor 18B to the controller 24. Thus, during operation of the monopolar instrument 16, energy flows from an active terminal 22B of the energy source 22 to monopolar instrument 16 via conductor 18A and returns to energy source 22 via the return pad 20 and return terminal 22A. The controller 24 also receives information, e.g., data from the monopolar instrument 16 regarding tissue parameters or instrument parameters, via the conductor 18B. The controller 24 may actuate switches 26 and 28 based on a user input or based on information stored on the monopolar instrument 16 that is transmitted to the controller 24 when the monopolar instrument 16 is initially connected to the electrosurgical generator 12.

When the bipolar instrument 14 is connected to the electrosurgical generator 12, the controller 24 actuates the switch 26 to connect the return terminal 22A of the energy source 22 to the conductor 30 while the switch 28 is actuated to connect the conductor 18B to the conductor 30. Thus during operation of the bipolar instrument 14, energy flows from the active terminal 22A of the energy source 22 to the bipolar instrument 16 via the conductor 18A and returns to the energy source 22 via the conductor 18B, the conductor 30, and the return terminal 22B. The controller 24 may actuate the switches 26 and 28 based on a user input or based on information stored on the bipolar instrument 14 that is transmitted to the controller 24 when the bipolar instrument 14 is initially connected to the electrosurgical generator 12.

Figure 2:
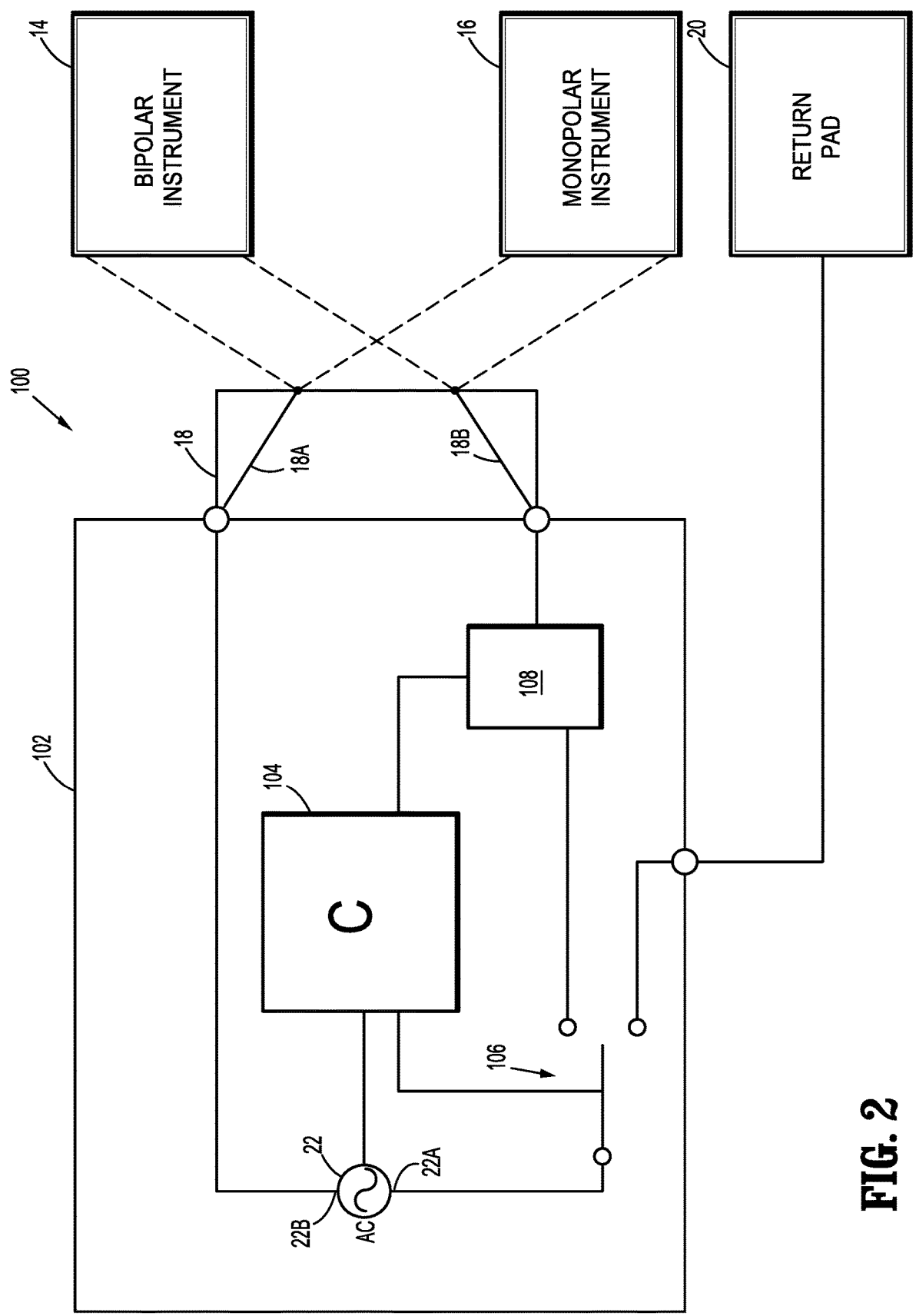
FIG. 2 is a block diagram of an electrosurgical system using a common conductor in accordance with another embodiment of the present disclosure.

Turning to FIG. 2, an electrosurgical system in accordance with an embodiment of the present disclosure is shown generally as 100. Electrosurgical system 100 includes an electrosurgical generator 102 that may be connected to the bipolar instrument 14 or the monopolar instrument 16 via the cable 18. A return pad 20 may be connected to the electrosurgical generator 102 when the monopolar instrument 16 is connected to the electrosurgical generator 102.

The electrosurgical generator 102 includes energy source 22 and a controller 104 that controls the output of energy source 22 based on the type of therapy (i.e., sealing, cutting, cauterizing, etc.) being applied to tissue by the instrument 14 or 16.

When the monopolar instrument 16 is connected to the electrosurgical generator 102, the controller 104 actuates switch 106 to connect the return terminal 22A of the energy source 22 to the return pad 20. Thus, during operation of the monopolar instrument 16, energy flows from the active terminal 22B of the energy source 22 to monopolar instrument 16 via conductor 18A and returns to the return terminal 22A of the energy source 22 via the return pad 20. The electrosurgical generator 102 also includes a demultiplexer 108 that receives information, e.g., data from the monopolar instrument 16 regarding tissue parameters or instrument parameters, via the conductor 18B and provides the information to controller 104. The controller 108 may actuate switch 106 based on a user input or based on information stored on the monopolar instrument 16 that is transmitted to the controller 104 when the monopolar instrument 16 is initially connected to the electrosurgical generator 12.

When the bipolar instrument 14 is connected to the electrosurgical generator 102, the controller 104 actuates the switch 106 to connect the return terminal 22A of the energy source 22 to the multiplexer 108. The controller 104 may actuate a switch 106 based on a user input or based on information stored on the bipolar instrument 14 that is transmitted to the controller 104 when the bipolar instrument 14 is initially connected to the electrosurgical generator 102. Thus during operation of the bipolar instrument 14, energy flows from the active terminal 22B of the energy source 22 to the bipolar instrument 16 via the conductor 18A and returns to the energy source 22 via the conductor 18B, the demultiplexer 108, and the return terminal 22A. The controller 104 may also query bipolar instrument 14 for tissue parameters or instrument parameters, via the demultiplexer 108 and conductor 18B. The demultiplexer 108 may use any conventional demultiplexing techniques to transmit/receive data and energy along conductor 18B. Demultiplexer 108 separates an incoming signal, which includes electrosurgical energy and data, from the bipolar instrument 14 and provides the data to controller 104 while returning the electrosurgical energy back to energy source 22 via the return terminal 22A.

Figure 3:
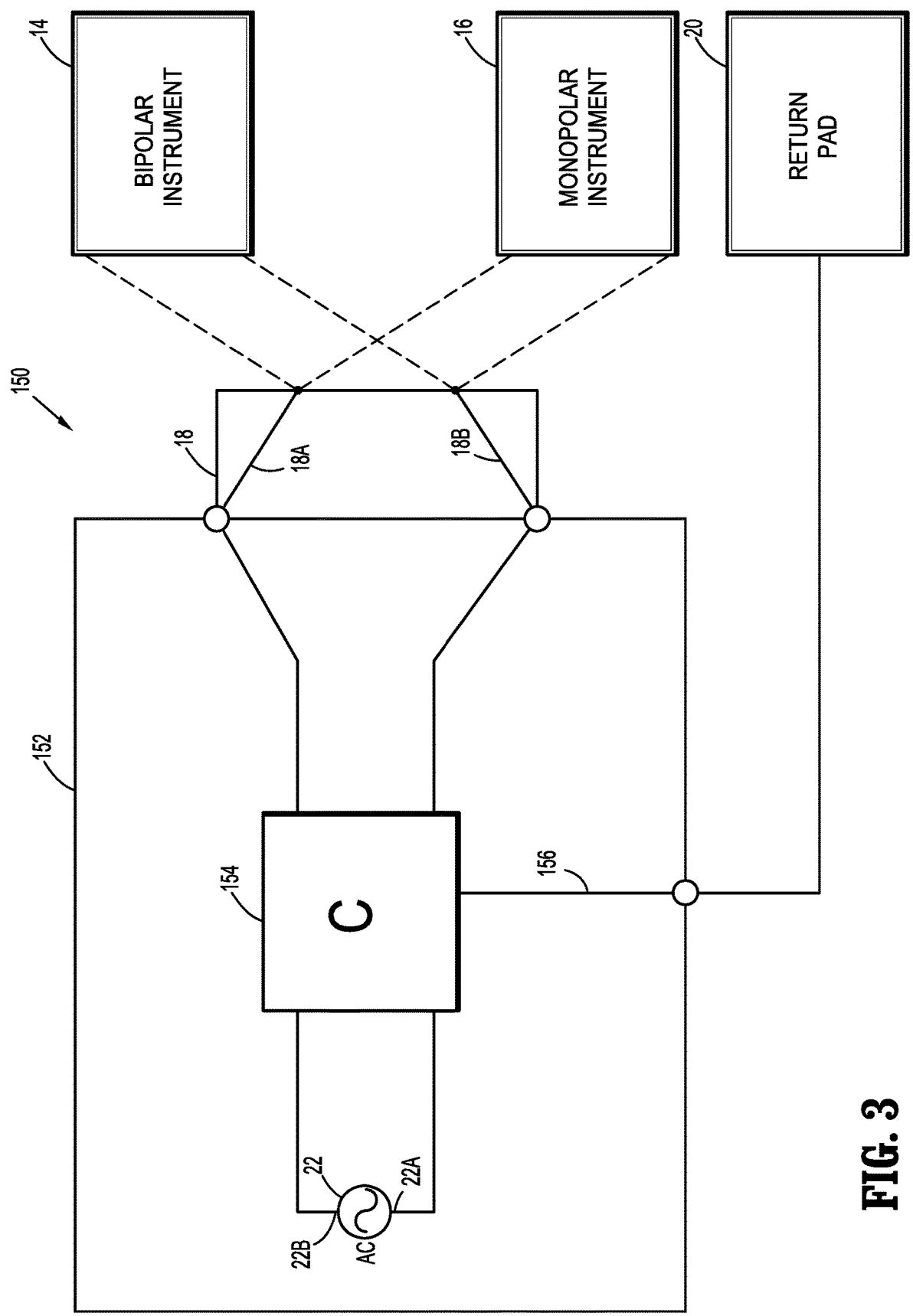
FIG. 3 is a block diagram of an electrosurgical system using a common conductor in accordance with another embodiment of the present disclosure.

Turning to FIG. 3, an electrosurgical system in accordance with an embodiment of the present disclosure is shown generally as 150. Electrosurgical system 150 includes an electrosurgical generator 152 that may be connected to the bipolar instrument 14 or the monopolar instrument 16 via the cable 18. A return pad 20 may be connected to the electrosurgical generator 152 when the monopolar instrument 16 is connected to the electrosurgical generator 152.

The electrosurgical generator 152 includes energy source 22 that is electrically coupled to controller 154 that controls the output of energy source 22 based on the type of therapy (i.e., sealing, cutting, cauterizing, etc.) being applied to tissue by the instrument 14 or 16. Based on whether the bipolar instrument 14 or the monopolar instrument 16 is connected to the electrosurgical generator 152, the controller 154 either electrically couples monopolar instrument 16 and return pad 20 to energy source 22 or electrically couples bipolar instrument 14 to energy source 22.

When the monopolar instrument 16 is initially connected to the electrosurgical generator 152, an instrument identification (ID) stored in monopolar instrument 16 is transmitted to controller 154 causing controller 154 to electrically couple the monopolar instrument 16 and the return pad 20 to the energy source 22 via conductor 18A and conductor 156. The controller 154 may also query monopolar instrument 16 for tissue parameters or instrument parameters via conductor 18B. When the bipolar instrument 14 is initially connected to the electrosurgical generator 152, an instrument ID stored in bipolar instrument 14 is transmitted to controller 154 causing controller 154 to electrically couple the bipolar instrument 14 to the energy source 22 via conductor 18A and conductor 18B. The controller 154 may also query bipolar instrument 14 for tissue parameters or instrument parameters via conductor 18A or 18B. The controller 154 may also use any conventional multiplexing techniques to transmit/receive data and energy along cable 18.

The above-described embodiments may also be configured to work with robotic surgical systems and what is commonly referred to as "Telesurgery." Such systems employ various robotic elements to assist the clinician in the operating theater and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include, remotely steerable systems, automatically flexible surgical systems, remotely flexible surgical systems, remotely articulating surgical systems, wireless surgical systems, modular or selectively configurable remotely operated surgical systems, etc.

Figure 4:
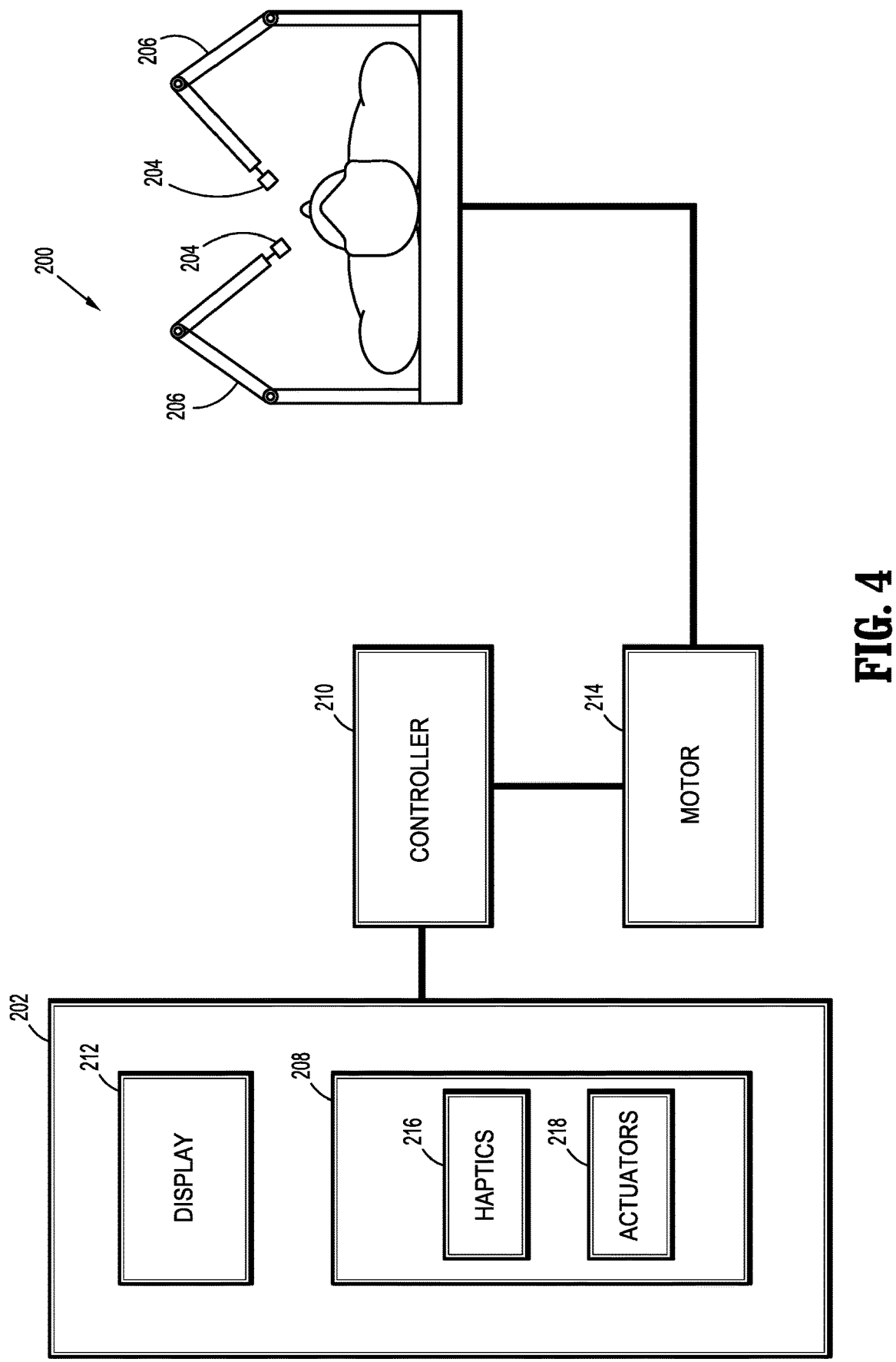
FIG. 4 is a block diagram of a robotic surgical system in accordance with an embodiment of the present disclosure.

As shown in FIG. 4, a robotic surgical system 200 may be employed with one or more consoles 202 that are next to the operating theater or located in a remote location. In this instance, one team of clinicians or nurses may prep the patient for surgery and configure the robotic surgical system 200 with one or more instruments 204 while another clinician (or group of clinicians) remotely controls the instruments via the robotic surgical system. As can be appreciated, a highly skilled clinician may perform multiple operations in multiple locations without leaving his/her remote console which can be both economically advantageous and a benefit to the patient or a series of patients.

The robotic arms 206 of the surgical system 200 are typically coupled to a pair of master handles 208 by a controller 210. Controller 210 may be integrated with the console 202 or provided as a standalone device within the operating theater. The handles 206 can be moved by the clinician to produce a corresponding movement of the working ends of any type of surgical instrument 204 (e.g., probe, end effectors, graspers, knifes, scissors, etc.) attached to the robotic arms 206.

The movement of the master handles 208 may be scaled so that the working ends have a corresponding movement that is different, smaller or larger, than the movement performed by the operating hands of the clinician. The scale factor or gearing ratio may be adjustable so that the operator can control the resolution of the working ends of the surgical instrument(s) 204.

During operation of the surgical system 200, the master handles 208 are operated by a clinician to produce a corresponding movement of the robotic arms 206 and/or surgical instruments 204. The master handles 208 provide a signal to the controller 210 which then provides a corresponding signal to one or more drive motors 214. The one or more drive motors 214 are coupled to the robotic arms 206 in order to move the robotic arms 206 and/or surgical instruments 204.

The master handles 208 may include various haptics 216 to provide feedback to the clinician relating to various tissue parameters or conditions, e.g., tissue resistance due to manipulation, cutting or otherwise treating, pressure by the instrument onto the tissue, tissue temperature, tissue impedance, etc. As can be appreciated, such haptics 216 provide the clinician with enhanced tactile feedback simulating actual operating conditions. The haptics 216 may include vibratory motors, electroactive polymers, piezoelectric devices, electrostatic devices, subsonic audio wave surface actuation devices, reverse-electrovibration, or any other device capable of providing a tactile feedback to a user. The master handles 208 may also include a variety of different actuators 218 for delicate tissue manipulation or treatment further enhancing the clinician's ability to mimic actual operating conditions.

The embodiments disclosed herein are examples of the disclosure and may be embodied in various forms. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

The phrases "in an embodiment," "in embodiments," "in some embodiments," or "in other embodiments," which may each refer to one or more of the same or different embodiments in accordance with the present disclosure. A phrase in the form "A or B" means "(A), (B), or (A and B)". A phrase in the form "at least one of A, B, or C" means "(A), (B), (C), (A and B), (A and C), (B and C), or (A, B and C)". A clinician may refer to a surgeon or any medical professional, such as a doctor, nurse, technician, medical assistant, or the like performing a medical procedure.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, or the like. The controller may also include a memory to store data and/or algorithms to perform a series of instructions.

Any of the herein described methods, programs, algorithms or codes may be converted to, or expressed in, a programming language or computer program. A "Programming Language" and "Computer Program" includes any language used to specify instructions to a computer, and includes (but is not limited to) these languages and their derivatives: Assembler, Basic, Batch files, BCPL, C, C+, C++, Delphi, Fortran, Java, JavaScript, Machine code, operating system command languages, Pascal, Perl, PL1, scripting languages, Visual Basic, metalanguages which themselves specify programs, and all first, second, third, fourth, and fifth generation computer languages. Also included are database and other data schemas, and any other metalanguages. No distinction is made between languages which are interpreted, compiled, or use both compiled and interpreted approaches. No distinction is also made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Any of the herein described methods, programs, algorithms or codes may be contained on one or more machine-readable media or memory. The term "memory" may include a mechanism that provides (e.g., stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

It should be understood that the foregoing description is only illustrative of the present disclosure. Various alternatives and modifications can be devised by those skilled in the art without departing from the disclosure. For instance, any of the augmented images described herein can be combined into a single augmented image to be displayed to a clinician. Accordingly, the present disclosure is intended to embrace all such alternatives, modifications and variances. The embodiments described with reference to the attached drawing figs. are presented only to demonstrate certain examples of the disclosure. Other elements, steps, methods and techniques that are insubstantially different from those described above and/or in the appended claims are also intended to be within the scope of the disclosure.

What is claimed is:

1. An electrosurgical system comprising:
   an electrosurgical instrument;
   an electrosurgical generator including:
      an energy source having an active terminal and a return terminal that outputs electrosurgical energy; and
      a controller that controls the energy source;
   a cable coupled between the electrosurgical instrument and the electrosurgical generator, the cable including a first conductor and a second conductor; and
   a demultiplexer,
   wherein the controller is configured to electrically couple at least one of the active terminal or the return terminal to the electrosurgical instrument using the respective the first conductor or the second conductor based on whether the electrosurgical instrument is a monopolar instrument or a bipolar instrument,
   wherein the monopolar instrument and the bipolar instrument are interchangeably coupled to a distal end of the cable, and
   wherein the demultiplexer:
      demultiplexes an incoming signal including the electrosurgical energy and a data signal from the bipolar instrument when the bipolar instrument is connected to the electrosurgical generator;
      provides the data signal to the controller; and
      returns the electrosurgical energy to the energy source.

2. The electrosurgical system of claim 1, wherein the controller electrically couples the return terminal to a return pad when the electrosurgical instrument is the monopolar instrument.

3. The electrosurgical system of claim 2, wherein the return terminal is electrically coupled to the return pad based on a signal transmitted along the second conductor from the monopolar instrument.

4. The electrosurgical system of claim 2, wherein the return terminal is electrically coupled to the return pad based on an input from a user.

5. The electrosurgical system of claim 2, further comprising:
   a first switch; and
   a second switch.

6. The electrosurgical system of claim 5, wherein the first switch electrically couples the return terminal to the return pad and the second switch electrically couples the second conductor to the controller when the electrosurgical instrument is the monopolar instrument.

7. The electrosurgical system of claim 5, wherein the first switch and the second switch couple the return terminal to the second conductor when the electrosurgical is the bipolar instrument.

8. The electrosurgical system of claim 5, wherein the first switch and/or the second switch are controlled by the controller based on data from the electrosurgical instrument.

9. The electrosurgical system of claim 1, wherein the second conductor is coupled to the controller when the electrosurgical instrument is the monopolar instrument.

10. The electrosurgical system of claim 1, wherein the controller electrically couples the return terminal to the electrosurgical instrument using the second conductor when the electrosurgical is the bipolar instrument.

11. The electrosurgical system of claim 1, wherein the controller electrically couples the return terminal to the second conductor based on a signal from the bipolar instrument.

12. The electrosurgical system of claim 1, wherein the return terminal is electrically coupled to the second conductor based on an input from a user.

13. An electrosurgical system comprising:
   an electrosurgical instrument;
   an electrosurgical generator including:
      an energy source having an active terminal and a return terminal that outputs electrosurgical energy; and
      a controller that controls the energy source; and
   a cable coupled between the electrosurgical instrument and the electrosurgical generator, the cable including a first conductor and a second conductor,
   wherein the controller is configured to electrically couple at least one of the active terminal or the return terminal to the electrosurgical instrument using the respective the first conductor or the second conductor based on whether the electrosurgical instrument is a monopolar instrument or a bipolar instrument,
   wherein the monopolar instrument and the bipolar instrument are interchangeably coupled to a distal end of the cable,
   wherein the controller includes a memory with instructions stored thereon which, when executed by the controller, cause the electrosurgical system to determine whether to electrically couple at least one of the active terminal or the return terminal to the electrosurgical instrument using the first conductor or the second conductor based on data stored on the electrosurgical instrument, and
   wherein the data stored on the instrument includes an indication that the electrosurgical instrument is a monopolar instrument or a bipolar instrument.

14. The electrosurgical system of claim 13, wherein the controller electrically couples the return terminal to a return pad when the electrosurgical instrument is the monopolar instrument.

15. The electrosurgical system of claim 14, wherein the return terminal is electrically coupled to the return pad based on a signal transmitted along the second conductor from the monopolar instrument.

16. The electrosurgical system of claim 14, wherein the return terminal is electrically coupled to the return pad based on an input from a user.

17. The electrosurgical system of claim 14, further comprising:
 a first switch; and
 a second switch.

18. The electrosurgical system of claim 17, wherein the first switch electrically couples the return terminal to the return pad and the second switch electrically couples the second conductor to the controller when the electrosurgical instrument is the monopolar instrument.

19. The electrosurgical system of claim 17, wherein the first switch and the second switch couple the return terminal to the second conductor when the electrosurgical is the bipolar instrument.

20. The electrosurgical system of claim 13, wherein the return terminal is electrically coupled to the second conductor based on an input from a user.

\* \* \* \* \*